United States Patent
Booker et al.

(10) Patent No.: US 10,541,056 B2
(45) Date of Patent: Jan. 21, 2020

(54) SYSTEM FOR COLLECTING AND DISPLAYING DIAGNOSTICS FROM DIAGNOSTIC INSTRUMENTS

(71) Applicant: Quidel Corporation, San Diego, CA (US)

(72) Inventors: David Dickson Booker, Albuquerque, NM (US); Cheryl Marie Miller, Evanston, IL (US)

(73) Assignee: Quidel Corporation, San Diego, CA (US)

(*) Notice: Subject to any disclaimer, the term of this patent is extended or adjusted under 35 U.S.C. 154(b) by 235 days.

(21) Appl. No.: 15/127,379

(22) PCT Filed: Mar. 20, 2015

(86) PCT No.: PCT/US2015/021731
§ 371 (c)(1),
(2) Date: Sep. 19, 2016

(87) PCT Pub. No.: WO2015/143309
PCT Pub. Date: Sep. 24, 2015

(65) Prior Publication Data
US 2017/0177724 A1    Jun. 22, 2017

Related U.S. Application Data

(60) Provisional application No. 61/968,160, filed on Mar. 20, 2014.

(51) Int. Cl.
*G16H 50/80*    (2018.01)
*G06F 16/951*   (2019.01)
(Continued)

(52) U.S. Cl.
CPC ....... *G16H 50/80* (2018.01); *G01N 33/48792* (2013.01); *G06F 16/951* (2019.01); *G16H 10/40* (2018.01)

(58) Field of Classification Search
CPC ........ G16H 50/80; G16H 10/40; G06F 19/00; G06F 17/30864; G01N 33/48792
See application file for complete search history.

(56) References Cited

U.S. PATENT DOCUMENTS

2004/0078219 A1* 4/2004 Kaylor ................ G06F 19/3418
                                                          705/2
2013/0066563 A1   3/2013 Hengstler et al.
(Continued)

FOREIGN PATENT DOCUMENTS

JP   2001-290889 A   10/2001
JP   2002-245173 A    8/2002
(Continued)

OTHER PUBLICATIONS

Sintchenko et al. (Arch Pathol Lab Med—vol. 133, Jun. 2009). (Year: 2009).*

(Continued)

*Primary Examiner* — Sally A Merkling
(74) *Attorney, Agent, or Firm* — McDermott Will & Emery LLP; Judy M. Mohr; Ricardo J. Claps

(57) ABSTRACT

A system including multiple diagnostic instruments, each diagnostic instrument including a detector that interacts with a test assay is provided. At least one diagnostic instrument is configured to automatically associate the test assay with multiple values to generate a diagnostic. The diagnostic may be stored within a memory of the diagnostic instrument, and the multiple values may be related to one or more of: a test assay identifier, a test assay result, a patient identifier, and a diagnostic instrument identifier. At least one diagnostic instrument in the system may be configured to transmit the diagnostic to a first server for storage. The first server being configured to generate a report based on the diagnostic from each diagnostic instrument for display on a second server or (Continued)

on an end-user workstation. Methods for use the above system are also provided.

19 Claims, 9 Drawing Sheets

(51) Int. Cl.
    *G16H 10/40*     (2018.01)
    *G01N 33/487*     (2006.01)

(56) References Cited

U.S. PATENT DOCUMENTS

2013/0230844 A1    9/2013    Egan et al.
2013/0230845 A1*    9/2013    Egan .................. G01N 33/5302
                                                                                                                 435/5

FOREIGN PATENT DOCUMENTS

JP            2012-010964 A     1/2012
WO    WO 2013/131052 A1    9/2013
WO    WO 2015/143309 A1    9/2015

OTHER PUBLICATIONS

International Search Report from International Application No. PCT/US2015/021731 dated Jun. 2, 2015, application now published as International Publication No. WO2015/143309 on Sep. 24, 2015.

\* cited by examiner

| Instrument Run Date | Serial# | Age | Operator | Assay | Organization | Facility | Country | State | County | Type | Result |
|---|---|---|---|---|---|---|---|---|---|---|---|
| 18-Oct-2013 18:23:00 | 00000005 | >85Y | Operator 1 | FluABR4 | Original Word… | Pyramids of Giza | US | IL | Boone County | Patient | ⊖ |
| 18-Oct-2013 15:39:32 | 00000005 | 5W | Operator 7 | FluABR4 | Original Word… | Pyramids of Giza | US | IL | Boone County | Patient | ⊖ |
| 18-Oct-2013 14:36:45 | 00000001 | 5W | Operator 7 | FluABR4 | Original Word… | Colossus of Rho… | US | FL | Sarasota County | Patient | ⊖ |
| 18-Oct-2013 14:14:45 | 00000002 | >85Y | Operator 1 | FluABR4 | Original Word… | Gardens of Bab… | US | PA | Blair County | Patient | ⊕ |
| 18-Oct-2013 14:14:45 | 00000002 | 5W | Operator 7 | FluABR4 | Original Word… | Gardens of Bab… | US | PA | Blair County | Patient | ⊕ |
| 18-Oct-2013 12:59:04 | 00000007 | >85Y | Operator 1 | FluABR4 | Original Word… | Temple of Arte… | US | PA | Little River Cou… | Patient | ⊖ |
| 18-Oct-2013 12:23:00 | 00000005 | 7Y | Operator 6 | FluABR4 | Original Word… | Pyramids of Giza | US | IL | Boone County | Patient | ⊖ |
| 18-Oct-2013 12:11:27 | 00000003 | 3Y | Operator 7 | FluABR4 | Original Word… | Lighthouse of Al… | US | CO | Denver County | Patient | ⊖ |
| 18-Oct-2013 11:53:41 | 00000002 | >85Y | Operator 7 | FluABR4 | Original Word… | Gardens of Bab… | US | PA | Blair County | Patient | ⊖ |
| 18-Oct-2013 10:12:25 | 00000001 | >85Y | Operator 7 | FluABR4 | Original Word… | Colossus of Rho… | US | FL | Sarasota County | Patient | ⊖ |
| 18-Oct-2013 09:41:05 | 00000005 | >85Y | Operator 4 | FluABR4 | Original Word… | Pyramids of Giza | US | IL | Boone County | Patient | ⊖ |

FIG. 6

SYSTEM FOR COLLECTING AND DISPLAYING DIAGNOSTICS FROM DIAGNOSTIC INSTRUMENTS

CROSS-REFERENCE TO RELATED APPLICATIONS

This application is a U.S. National Stage of International Patent Application No. PCT/US2015/021731, filed Mar. 20, 2015, which claims the benefit of U.S. Provisional Application No. 61/968,160, filed Mar. 20, 2014, each of which is incorporated by reference herein in its entirety.

TECHNICAL FIELD

The present disclosure is directed to networked systems for clinical diagnostics, surveillance, data analysis and reporting to health organizations. The systems described herein automate the process of generating a database containing current clinical diagnostic data and reporting clinical diagnostic results to concerned organizations and agencies in a timely manner.

BACKGROUND

Clinical diagnostics is a rapidly growing field of medicine which has been greatly facilitated by the explosive increase in the determination of pathogen structure including nucleic acid sequences (genomic sequence data) and proteomics. Coupled to this rapid increase in sequence knowledge has been the vast improvement of detection techniques, specifically, immunohistochemistry for the detection of proteins and nucleic acid amplification and detection for the detection of nucleic acids. To fully benefit from these improved detection methods, it is critical to automate, wherever possible, the various diagnostic methods. Such automation reduces the need for tedious tasks and high level personnel and reduces introduction of human error.

As the number of clinical diagnostic tests increases as well as the number of patients undergoing such tests, the task of collecting and storing the resultant data has increasing importance and difficulty. Not only do the data need to be stored for current and later use, the data need to readily accessible and easy to manipulate by pertinent parties.

As explained by the Centers for Disease Control and Prevention (CDC), Electronic Laboratory Reporting (ELR) is the automated transmission of laboratory-related data from commercial, public health, hospital, and other labs to state and local public health departments thorough an electronic health records (EHR) system or a Laboratory Information Management System (LIMS). ELR helps identify reportable conditions determined by confirmatory testing and supports case reporting at the state or local level. ELR is used by laboratory providers to help them meet state reportable diseases laws mandating that providers report cases of specified diseases to the health department. ELR supports overall public health surveillance by helping improve the timeliness and accuracy of case reporting and confirmation to state and local health departments. It also supports national public health surveillance by improving the timeliness and accuracy of notifiable disease data voluntarily shared by states with CDC.

Accordingly, there is a great need for means by which clinical diagnostic data can be collected, maintained and transmitted. Of greater importance is the need for these data to remain secure and confidential. Preferably, these tasks require minimal human intervention and maintenance.

BRIEF SUMMARY

The foregoing examples of the related art and limitations related therewith are intended to be illustrative and not exclusive. Other limitations of the related art will become apparent to those of skill in the art upon a reading of the specification and a study of the drawings.

In one aspect, a disease surveillance system that is capable of near real-time disease surveillance is provided. In one embodiment, the system comprises a diagnostic instrument, a router, and a first server that, collectively, perform and transmit results of one or more clinical diagnostic assays. In another embodiment, the system additionally comprises a second server. The diagnostic instrument, in one embodiment, has a detector that interacts with a test assay to perform a diagnostic test and software to generate a result or a data set that can be stored within the diagnostic instrument, for example on the instrument hard drive, and/or on a removable storage device. The router transmits the result or the data set from the diagnostic instrument to the first server which houses a first database which is configured to store a plurality of the data sets. In one embodiment, the first server is in a geographic location that is remote from the geographic location of the diagnostic instrument. In another embodiment the data set is transmitted from the router to the first server via a cellular signal or through an internet connection.

In embodiments where the system includes a second server, the data set is then transmitted to the second server which houses a second database which is configured to store a plurality of the data sets. In one embodiment, the second server is in a geographic location that is remote from the geographic location of the first server and/or a diagnostic instrument.

In one embodiment, the second server comprises an application which queries the first server regarding the presence of one or more new data sets since the previous query and initiates transfer of the one or more new data sets to the second server.

In one embodiment, the second server comprises an application which generates a diagnostic surveillance report which is transmitted to a customer reporting database housed on a third server or on an end user workstation. The end user workstation may be, for example, part of a health department disease surveillance system. The third server may be, for example, at a geographic location remote from the first server, the second server, and/or the end user workstation.

In one embodiment, the diagnostic instrument performs a diagnostic assay and generates a data set comprising a result from the assay and diagnostic assay-associated data elements, such as a patient identifier, a diagnostic instrument identifier, an owner of the diagnostic instrument identifier, an identifier of the geographic location of the diagnostic instrument, and the like. In another embodiment, the data set is encrypted and transmitted to the router. In another embodiment, the patient identifier data element is masked or deleted in order to provide a de-identified data set for compliance with regulations to de-identify the patient associated with a single diagnostic assay or result in the data set. In one embodiment, the identifier of the geographic location of the diagnostic instrument is a zip code. In another embodiment, the assay-associated data element is a zip code of the residence of the patient and/or the location of the diagnostic instrument.

In one embodiment, the diagnostic instrument is any apparatus which is capable of performing a clinical diagnostic test assay, analyzing the results of the assay and converting the results to a digital signal which can be saved to and/or transmitted to, for example, a router, a server or a computer system. In one embodiment, the clinical diagnostic assay is an immunofluorescent assay. In another embodiment, the assay is an amplification assay, using for example polymer chain reaction (PCR) or an isothermal amplification such as helicase dependent amplification, where for example a dye or fluorescent label is detected.

In another aspect, a process by which a clinical diagnostic test is performed and the results are transmitted to an end user computer is provided.

In yet another aspect, a system for disease surveillance is provided, where the system comprises a diagnostic instrument comprising a detector that interacts with a diagnostic assay. The diagnostic instrument is configured to (i) automatically associate a diagnostic assay with multiple values to generate a data set, the data set stored within a memory of the diagnostic instrument, the multiple values related to one or more of: a patient identifier, a diagnostic instrument identifier, an owner of the diagnostic instrument identifier, and a geographic location of the diagnostic instrument; and (ii) transmit the data set to a first server via a router for storage at the first server. A server in the system generates a diagnostic report based on the data set for transmission to a database housed on a database server or on an end-user workstation.

In one embodiment, the router comprises an application with encrypts the data set. In another embodiment, the router receives the data set from the diagnostic instrument and then transmits the data set to the first server.

In another embodiment, the first server comprises a first database which is designed to store multiple data sets generated by the diagnostic instrument.

In still another embodiment, the end-user workstation comprises an application which allows the end-user workstation to query the database.

In one embodiment, the system further comprises a second server that receives the data set transmitted by the first server, wherein the second server comprises a second database comprised of multiple data sets generated by the diagnostic instrument.

In yet another embodiment, the end-user workstation comprises an application which allows the end-user to query the second database. In another embodiment, an end-user can access the data set on the first or the second server via an internet browser.

In still another embodiment, the second server and/or the first server comprise a reporting application which transmits a diagnostic report to the end-user computer, wherein the diagnostic report comprises a plurality of data sets, and wherein the end-user computer comprises a database configured to receive the diagnostic report or the end-user computer permits access to the diagnostic report using a internet tool, such as a browser application.

In another embodiment, the system comprises multiple diagnostic instruments.

In another aspect, a system for disease surveillance is provided. The system comprises a) one or more diagnostic instruments, each comprising a detector to interact with a test assay that receives a patient sample and software to analyze and store results detected by the detector as it interacts with the test assay to generate a data set, wherein the data set comprises a plurality of assay-associated data elements including at least a diagnostic instrument owner identifier, a diagnostic instrument identifier, and a test assay result; and b) a first server comprising a first database which stores a first plurality of the data sets received from the one or more diagnostic instruments, wherein for each of the data sets, each of the first plurality of the data sets is saved to the first database and wherein a unique identifier is assigned to each of the first plurality of data sets to generate a second plurality of the data sets.

In one embodiment, the system further comprises a second server comprising a second database which stores a second plurality of the data sets, and wherein the second server comprises a query generation program configured to generate a plurality of diagnostic information queries specific to an assay-associated data element in the plurality of assay-associated data; and wherein the query generation program generates a diagnostic report containing one or more diagnostic assay-associated data elements based on the plurality of diagnostic information queries.

In one embodiment, the system further comprises one or more routers, wherein each of the data sets is transmitted from the one or more diagnostic instruments to the one or more routers, and then to the first server.

In another embodiment, the system further comprises a workstation which stores a laboratory information system (LIS), wherein the workstation is connected to one or more of the one or more diagnostic instruments via a local area network.

In yet another embodiment, the plurality of diagnostic assay-associated data elements includes a residence or zip code of the patient or of the diagnostic instrument's location, age of the patient, and/or gender of the patient. In still another embodiment, the diagnostic report is generated in the form of a geographic map based on the residence or zip code of the patient.

In another aspect, a method for generating and reporting data sets comprising diagnostic information related to an infectious agent is provided. The method comprises a) inputting information regarding a clinical diagnostic assay and identification data for a patient into a diagnostic instrument, the diagnostic instrument comprising a detector that interacts with a test assay; b) running, on the diagnostic instrument, the test assay with a sample from the patient to obtain an assay test result; c) with the diagnostic instrument, storing the assay test result in combination with the patient identification data to generate a data set; d) transmitting the data set from the diagnostic instrument to a router; and e) transmitting the data set from the router to a first server, wherein the first server comprises a first database configured to store a plurality of the data sets. The data set is added to a first database; and the server or an end-user workstation or end-user server comprises an application which queries the first server for the presence of a new data set in the first database and initiates transfer of the new data set, if present, to the end-user workstation or end-user server.

In one embodiment, the method further comprises f) transmitting the data set from the router to a second server, wherein the second server comprises a second database configured to store a plurality of the data sets, wherein the data set is added to the second database, wherein the second server comprises a query generation program configured to generate a plurality of diagnostic information queries specific to a diagnostic instrument owner identifier; and wherein the query generation program generates a diagnostic report containing one or more diagnostic assay-associated data elements based on the plurality of diagnostic information queries.

In another embodiment, the method further comprises encrypting the data set prior to transmitting the data set from the diagnostic instrument to the router.

In another embodiment, the identification data for a patient includes a patient unique identifier and wherein the data set is processed by an application to remove the patient unique identifier from the data set prior to transmitting the data set to the router.

In another embodiment, the method further comprises generating an auto-reporting data set from the first database or the second database and transmitting the auto-reporting data set to a health information database located on an end-user workstation.

Additional embodiments of the present system and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE FIGURES

FIG. 6 shows an embodiment of an interface with a database on a server.

DETAILED DESCRIPTION

Figure 1:
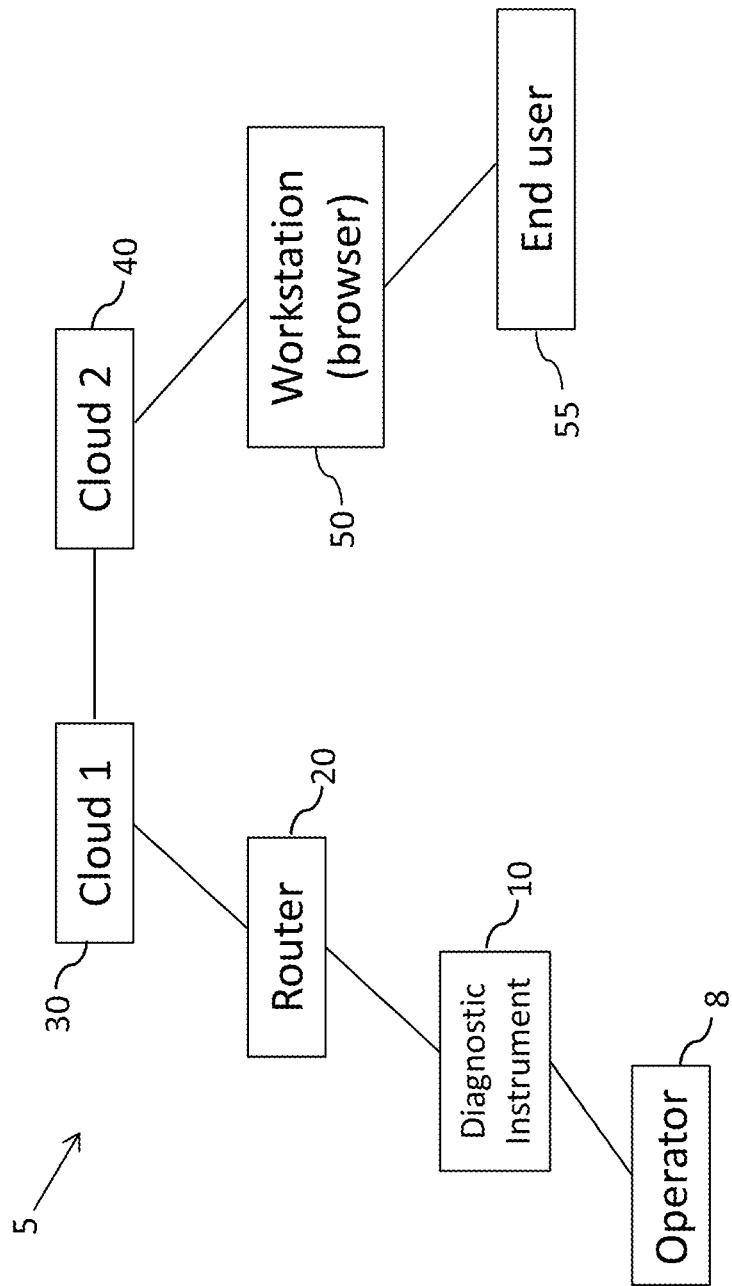
FIG. 1 is a block diagram of a system in accordance with the present disclosure.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. DEFINITIONS

As used in this specification, the singular forms "a," "an," and "the" include plural referents unless the context clearly dictates otherwise. Thus, for example, reference to a "computer" includes a single computer as well as two or more of the same or different computers.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

As used herein, "data" is used generically and includes but is not limited to information in a form suitable for processing by a computer. Except where noted otherwise, "data" is information (including operational and legacy) which is contained or capable of being contained in a data source (as defined below). For example, "data," includes but is not limited to individual patient information such as height, weight, sex and age; diagnostic instrument information such as owner and serial number; and diagnostic test data such as lot number and time of testing. A "data set" is a collection of data wherein all individual data within a data set originated from a single diagnostic test.

As used herein, a "diagnostic instrument" is any apparatus or device which can perform a diagnostic test on a sample obtained from a subject, analyze the results, and convert the results to data which is suitable for processing by a computer. A diagnostic instrument includes but is not limited to one that reads results as positive or negative, or one which quantifies the results to provide a quantitative value to the results.

As used herein, "database" is used generically and includes but is not limited to a database and/or software application which provides and/or stores data. For example a "database" contains information relating to a clinical diagnostic test, diagnostic instrument, site, study, patient or any other entity related to the clinical diagnostics industry.

II. DISEASE SURVEILLANCE SYSTEM

The present disclosure provides methods and systems for detecting, recording and reporting information related to the incidence and spread of disease among a population. Also provided are means for efficient, useful and controlled access to the information by persons or agencies of interest.

FIG. 1 illustrates an embodiment of a disease surveillance system 5 which includes at least one diagnostic instrument 10, a router 20, a first remote server 30, a second remote server 40, and an end-user device 50. Diagnostic instrument 10 functions to read a diagnostic test strip or device, as described in more detail below, analyze the results, encrypt at least a portion of the results, and transmit the results to router 20. Transmission of data from diagnostic instrument 10 to router 20 is preferably done through a physical connection (e.g., wire or cable), but may optionally be done via a wireless connection. The data are transferred from router 20 to first remote server 30 though a cellular connection. In some embodiments, the data are transmitted from router 20 to first remote server 30 through an internet connection (E.g., Ethernet or fiber optic cable). The transmission is secure via SSL TCP/IP. An application located on second remote server 40 is programmed to retrieve data which are temporarily stored on first remote server 30. The application can be programmed to identify and retrieve only data which are new, i.e., which have not previously been retrieved by the application.

Data which were generated using diagnostic instrument 10 and transmitted to second remote server 40 are stored on second remote server 40 in a database which has restricted access to parties as determined by the owner of diagnostic instrument 10. The database on second remote server 40 is configured such that it can be queried by a remote user to generate a reporting data set. Second remote server 40 can also house an application programmed to generate and send to an end user device a data report. The data report is one which contains data according to specifications set by the owner of the data sets generated by one or more diagnostic instruments 10 or by a user 55 and/or administrator of end user device such as a workstation having a browser application. End user device 50 may include an application which can receive data which is transmitted from second remote server 40 in the absence of a query from end user device 40. In this embodiment, an application on second remote server 40 is programmed to send data to end user device 50 according to specifications (data types, frequency of transmission) set by a user or administrator of end user device 50. End user device 50 includes any device which is configured to run an application which can query the data stored on second remote server 40 or which houses a database which can receive and store data obtained from the database on second remote server 40. An application on remote server 40 can generate a data report and send the data report to multiple end user devices as determined by the owner of the data in the data report. In another embodiment, an end-user can access the data set on the first or the second server via an internet browser.

A disease surveillance system as described above is designed to allow connection and management of one or of multiple diagnostic instruments. For example, tens, hundreds, thousands, tens of thousands or more diagnostic instruments, such as those described below, are each connected via one or more routers to a first remote server. Each diagnostic instrument is designed to run and analyze a diagnostic assay, wherein little or no human interaction with the diagnostic instrument occurs after a patient sample is introduced to the diagnostic instrument. The diagnostic instruments may be located anywhere within a country or within the world as long as the router is capable of transmitting new data sets to a first remote server.

Figure 2:
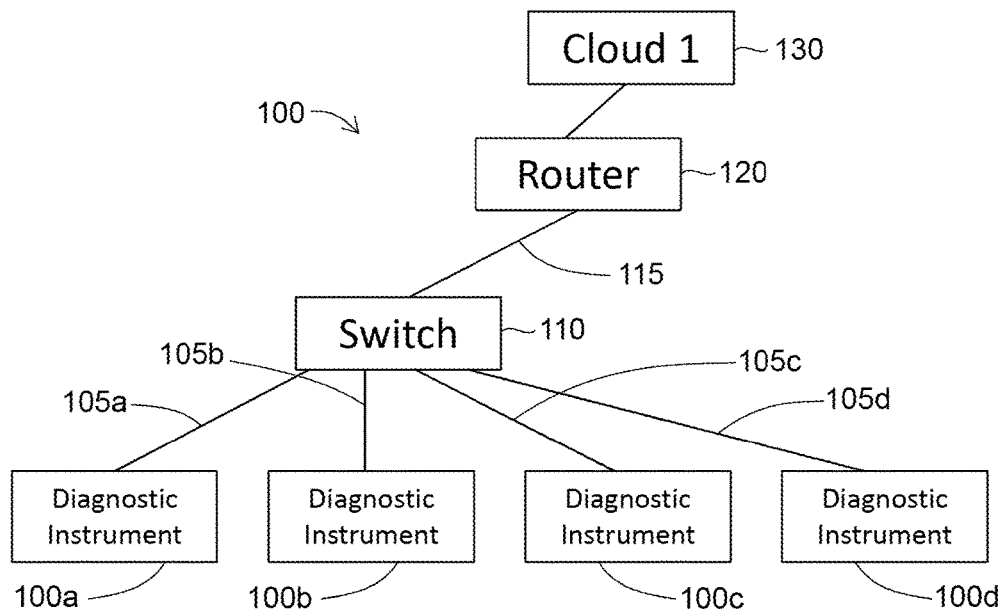
FIG. 2 is a block diagram of a system in accordance with the present disclosure wherein several diagnostic instruments are connected to a router.

The disease surveillance system described above and herein can include alternative configurations. In one embodiment, as shown in FIG. 2, a surveillance system 100 includes one or more diagnostic instruments (E.g., 100a, 100b, 100c, 100d) which are each connected to a hub or switch 110 by way of a wired connection 105a, 105b, 105c, 105d. The connection between each diagnostic instrument 100a-b and hub or switch 110 can be a cable connection or a wireless connection. A cable then connects hub or switch 110 to a single router 120 by a wire 115. Router 120 is then connected to a first remote server 130, by way of a cellular or cable/internet connection.

Figure 3:
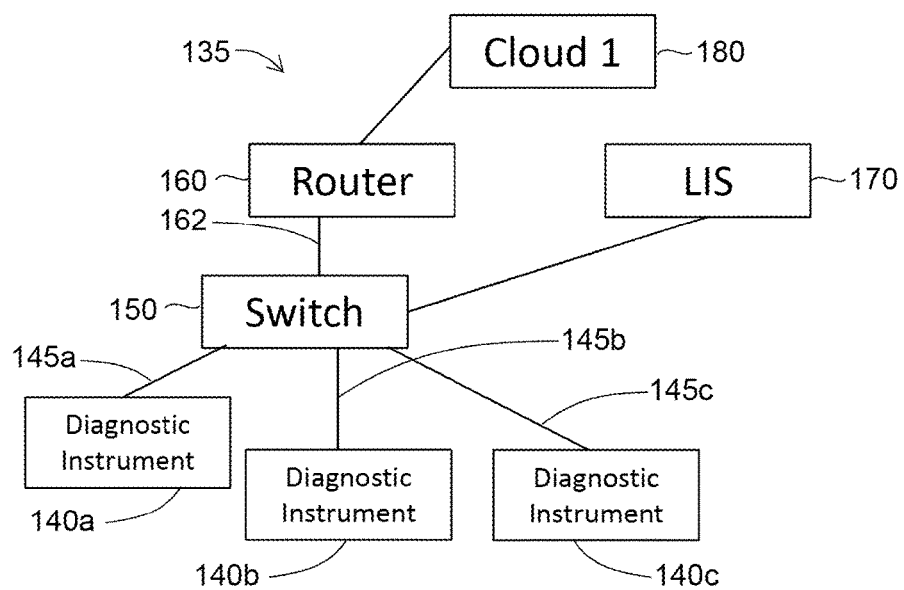
FIG. 3 is a block diagram of a system in accordance with the present disclosure wherein several diagnostic instruments are connected to a router and an LIS.

Another configuration of a networked system 135 includes a workstation which houses a Library Information Management System (LIMS). As shown in FIG. 3, one or more diagnostic instruments 140a, 140b, 140c within a clinical laboratory, for example, are each connected by a wire 145a, 145b, 145c to a hub or switch 150. Hub or switch 150 is then connected to a personal computer or workstation 170 which can house a LIMS. Hub or switch 150 can also be connected by a cable 162 to a router 160. Router 160 is connected to a first remote server 180, by way of a cellular or cable/internet connection.

The embodiments illustrated in FIGS. 2 and 3 are exemplary embodiments which may be varied according to need. Either one or more than one diagnostic instrument can be connected to the switch. The apparatus shown as a switch may also be a hub. The connection between the diagnostic instrument and the switch or hub may be a wired connection such as an Ethernet cable. The connection between the switch or hub and the router may be any appropriate wired connection.

When the system is configured to include a workstation having a Library Information System (LIS), there is a connection between each diagnostic instrument and the workstation, and between each diagnostic instrument and the router. In some embodiments, there is a wire or cable connecting the router directly to the LIS as shown in FIG. 3. In such an embodiment, there may be no direct connection between the router and the LIS workstation (no wire connected to the router and to the LIS workstation). FIG. 3 shows that router 160 is connected directly to the LIS workstation. This direct connection is optional. Router 160 is connected to a first remote server via a cellular signal. In an alternative embodiment, the LIS is connected to a first remote server such as first remote server 180 in FIG. 3 via a wired internet cable such as an ethernet cable or a fiber optic cable.

An ordinarily skilled artisan understands that a variety of connection means can be used to connect the diagnostic instruments to one another, to an LIS and/or to a router. In an alternative embodiment, there is a connection between the switch or hub and the LIS, and a connection between the switch or hub and the router. As an example, one clinical laboratory may have eight diagnostic instruments, each capable of performing a unique diagnostic test, wherein all eight diagnostic instruments are connected to a single router. A second clinical laboratory may have five diagnostic instruments connected to a first router in one room, and seven diagnostic instruments connected to a second router in a second room. Each of the first and second routers connects via a cellular signal to a first remote server, in which data and information from all twelve diagnostic instruments in the first and second rooms are stored. The first and second clinical laboratories may be located, for example, in different towns, different states, or different countries assuming compatibility of the all routers with the first remote server. Data saved to the first remote server is then transferred to a second remote server. One or more devices, such as a computer, work station, or hand held device, each of which may be located in a different town, state or country for example, is capable of accessing the second remote server to query or browse the data held there, based on permissions granted a user.

The system as described herein is designed to allow, in part, automated and secure transmission of results generated by a diagnostic instrument to a router, a first remote server, then to a second remote server. Each result from a single diagnostic assay is automatically associated with multiple values related to the patient, the diagnostic instrument and the owner of the diagnostic instrument to generate a data set which is then stored within the memory of the diagnostic instrument. For example, a positive result from a single diagnostic assay is saved in association with instrument data such as an instrument identification number and laboratory affiliation, and patient information such as patient age and place of residence. In this way, for example, by automatically associating each result from a single diagnostic assay with multiple values related to the patient, the functioning of the diagnostic instrument is improved. As an illustrative and non-limiting example, such improvement may include less memory use and faster processing by the diagnostic instrument. It is to be appreciated that these example improvements are not limited to the diagnostic instrument and may occur at other components (e.g., servers, routers, end-user computers etc.) associated with the diagnostic instrument. Each data set is then transmitted to the first remote server via a router. Before each data set is transmitted, the data are encrypted using a program within the diagnostic instrument. Additionally, the diagnostic instrument administrator and/or user may program the diagnostic instrument to generate a data set for transmission which omits or masks, for example, the patient identification number.

A diagnostic instrument, such as that which is depicted in FIG. 1 (10) and FIGS. 2 (100a-d, 130 and 170), which may be used in any of the networked systems described herein includes any which can at least: 1) accept data input by an operator or user via a user interface such as a keyboard, a key pad, or a barcode reader; 2) accept a test strip which carries out a diagnostic test in the presence of a sample; 3) a detector such as an optical reader which generates and detects a light signal in the presence of the test strip, and converts the optical data into digital data that can be stored on a memory device and analyzed; 4) a processor with software which can process the digital data to generate a result; and 4) an output mechanism which can send data and/or results generated though use and analysis of the test strip to an external storage device or server. Such diagnostic instruments are well known in the art and each is designed to analyze a specific chemical assay which has been designed to detect the presence of a disease-associated analyte or infectious disease agent. In the present disclosure, the diagnostic instrument does not require operator activity from the time the test strip has been introduced into the instrument until the time the data are accessed by the operator or other user.

An exemplary embodiment of a diagnostic instrument for use with the herein described networked surveillance system is disclosed in detail in U.S. Patent Pub. No. 2013/0230845, the contents of which are incorporated herein by reference in their entirety.

Figure 4A:
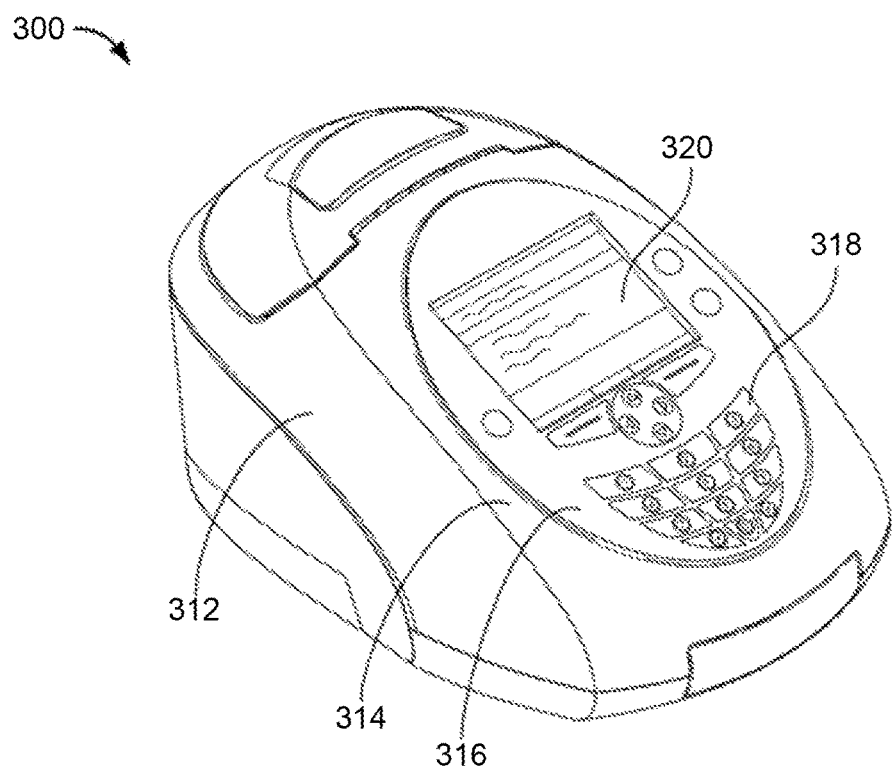
FIGS. 4A and 4B show an embodiment of a diagnostic instrument.
Figure 4B:
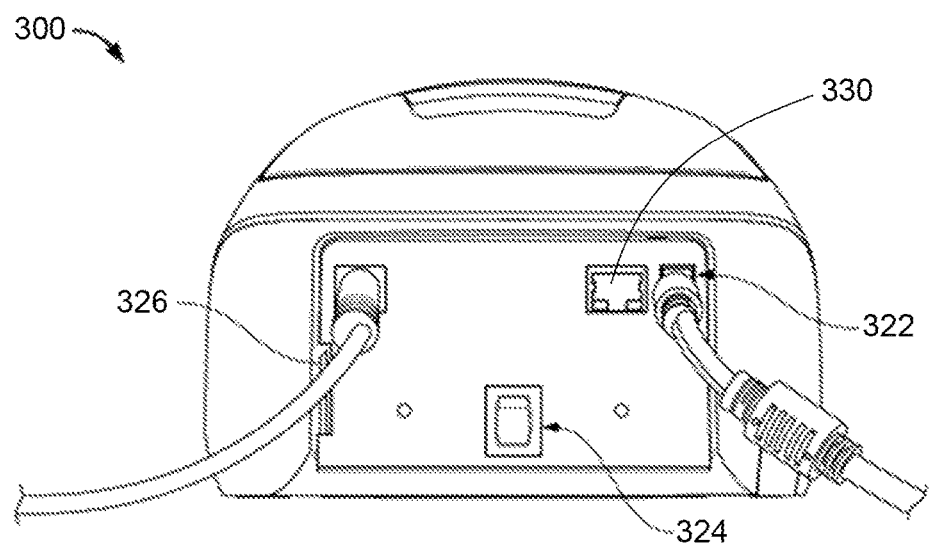

An embodiment of an apparatus capable of detecting a signal produced by a test device is illustrated in FIGS. 4A-4B. Diagnostic instrument 300 includes a housing 312 that encloses an optics system, electronics software, and other components of the diagnostic instrument. A front side 314 of the diagnostic instrument includes a user interface 316 that may include, for example, a key pad 318 and a display screen 320. The key pad includes numeric keys for entry of numeric values, which can also be labeled with letters of the alphabet, a decimal point key, a back space key, and other keys that are desired by end users. As part of the key pad or as separate keys positioned elsewhere on the diagnostic instrument, the device may include keys to print test results, to advance printer paper, to open or close a drawer in the device, directional arrow keys and soft or select keys for a user to interact and instruct the apparatus. Visible on display screen 320 to a user will be information such as test results, error messages, instructions, calibration information, troubleshooting information, user information, and the like.

An embodiment of the rear panel of diagnostic instrument 300 is shown in FIG. 4B and can include port to receive a source of AC power 322 and an on/off toggle switch 324, which in this embodiment is a soft key to activate the software. The diagnostic instrument additionally provides ports, on the rear panel or elsewhere on the apparatus, to connect optional components and/or to interface with external instruments. For example, the diagnostic instrument may include a PS2 connector, for example, to interface with an external barcode reader; a port, such as an RJ-45 port (e.g., FIG. 4B port 330), to connect to a local area network or Ethernet; a removable memory card port or slot; and/or a USB port. In a preferred embodiment, the diagnostic instrument includes a slot or port 326 for insertion of a removable non-volatile flash memory card, such as an SD card, and the diagnostic instrument is capable of read and write operations to and from the SD card, to, for example, store all scan data from each test strip, or to update system software.

The diagnostic instrument is equipped with ports for attachment to optional external devices, and in one embodiment the diagnostic instrument is connected to an external bar code scanner. The bar code scanner interfaces with the apparatus via a suitable data port provided on the diagnostic instrument. Externally attached devices ease transfer of data into and from the apparatus, and can eliminate user keyboard input, permitting accurate data input into the apparatus regarding a test to be analyzed or patient or sample information. In one embodiment, a barcode scanner external is attachable via PS-2 port on the apparatus and is capable of reading a linear or 1D bar code.

Hardware components of diagnostic device 300 further include an inter IC Bus (also known as the I2C-Bus, this component facilitates communication between electronic components), serial interface bus (SPI Bus), batteries, electronics, optional internal barcode reader and SD card.

Diagnostic instrument 300 is able to run diagnostic tests, as well as quality control (QC) tests and calibration assays.

The systems described herein are useful for the transmission, recording and reporting of data generated using a variety of diagnostic instruments. A diagnostic instrument useful in the presently described systems is any instrument which is capable of reading the results of an analytical assay, whether the results of the assay are simply positive or negative or are measured on a more quantitative scale. Examples of such diagnostic instruments include but are not limited to instruments which perform immunoassays and PCR. The diagnostic instrument may be any instrument which can read results of a test strip containing a patient or control sample and provide an automated determination of whether the test strip rendered a positive or negative result. In one embodiment, the diagnostic instrument is one which provides a qualitative test result, such as a number on a scale of 1 to 10 or 1 to 100. The diagnostic instrument is one which can convert the assay test results to a digital signal which can be transmitted via, e.g., the internet, a wireless signal, a cellular signal, etc.

Figure 5:
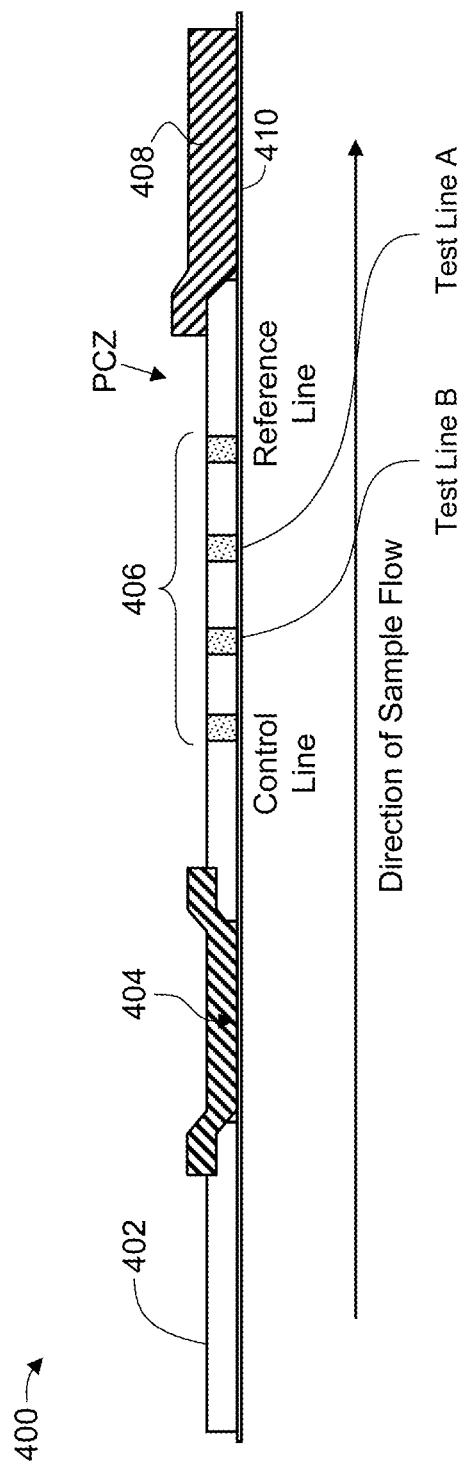
FIG. 5 shows an embodiment of an assay test strip.
Figure 8A:
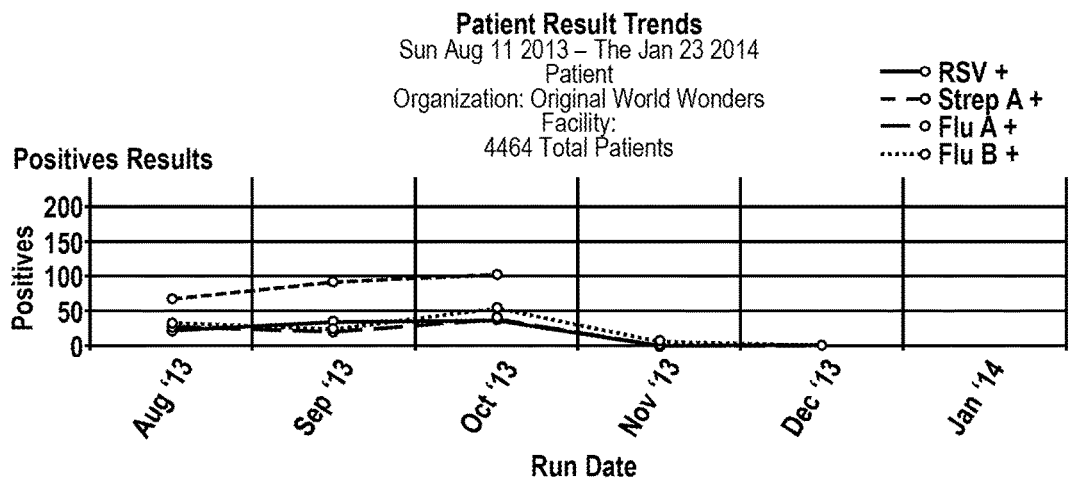
FIGS. 8A and 8B shows an embodiment of output generated from a database on a server.
Figure 8B:
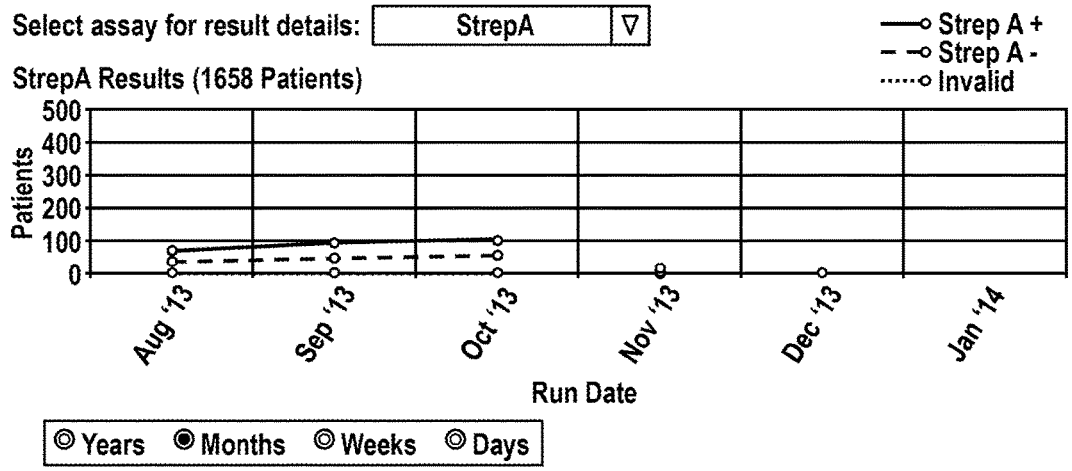

In one embodiment, the diagnostic instrument is designed for use with a lateral flow test strip and the diagnostic instrument implements a lateral flow reader function. An exemplary lateral flow immunoassay test strip is described in U.S. Patent Pub. No. 2013/0230844 (see, for example, paragraphs [0078-0085] and FIGS. 8-10, the contents of which are incorporated herein by reference in their entirety). With reference to FIG. 5, an embodiment of a test strip for interaction with the diagnostic instrument is illustrated. The test strip is exemplified in the drawings below by a lateral flow test immunoassay, however it will be appreciated that a lateral flow immunoassay is exemplary of test strips suitable for interaction with the apparatus. Test strip 400 is comprised of, in sequence, a sample pad 402, a label pad 404, one or more lines indicated collectively at 406 and selected from a test line, a control line and a reference line, and an absorbent pad 408. In one embodiment, a support member 410 is provided, and each or some of the sample pad, label pad, lines and absorbent pad are disposed on the support member. The test strip comprises a region between the downstream edge of the most downstream analyte-specific test line, which in the embodiment shown in FIG. 5 is test line for binding to an influenza antigen (e.g., a test line that comprises anti-flu A antibodies), and the upstream edge of the absorbent pad 408 is a procedural control zone, denoted PCZ in FIG. 5.

In one embodiment, the test strip is enclosed in a housing, sometimes referred to as a cassette. A bar code label can be affixed to the housing and positions for interaction with an internal bar code scanner positioned within the diagnostic instrument. In one embodiment, the bar code label is a 2D bar code, encoding information, for example, regarding the assay test strip, such as the pathogen/analyte the test strip is designed to detect (e.g., Flu A/B, Strep A, RSV, etc.) which informs the diagnostic instrument what protocol in memory to initiate for scanning the test strip; a unique test serial number so that the diagnostic instrument will not read same test strip twice. In one embodiment, the information contained in the bar code does not include information related to the patient or the sample type, and is limited to information about the test strip.

As described above, the presently disclosed systems are designed for efficient recordation, storage, retrieval and reporting of diagnostic data with minimal human interaction required. In one embodiment, a user must provide a sample and apply the sample to, for example, a test strip. Once the test strip with sample is placed within the diagnostic instrument and information regarding the patient and test strip is input into the instrument, no further user activity is required before the diagnostic test results are saved within the database on the second remote server or reported to an end user.

To initiate a scan of a test device, the diagnostic instrument is powered-on if needed and a toggle switch to initiate the diagnostic instrument software is activated. Prior to inserting the test strip with sample into the diagnostic instrument, using the optional external bar code reader, information about the user, the sample, the patient, etc. can be scanned into the diagnostic device memory. A "start test" button on the diagnostic instrument or on the touch screen is pressed to start a measurement of a test strip. The diagnostic instrument automatically opens the drawer in the apparatus to receive the test device on which a sample has been dispensed. The test device with loaded sample is inserted into the drawer of the diagnostic device and the drawer is closed.

Closure of the drawer initiates a sequence of events, comprised of the following. The internal bar code reader scans the bar code on the test device and receives information regarding the assay type (e.g., influenza A/B, Strep A, RSV, etc.), the serial number and the expiration date of the test device, optical cut-off information for the assay type, and any other information included on the bar code secured to the test device. It will be appreciated that the internal bar code reader is an optional feature, as the information on the bar code label can be entered into the apparatus by a user using the key pad or via an external bar code scanner.

At any time after the diagnostic instrument has been powered, an operator may enter information not obtained from the barcode on the test strip. For example, an operator can enter an identification number (operator ID), using either a keypad on the diagnostic instrument, or using a barcode reader. The device instrument operator can then enter patient information regarding the patient from whom a sample was obtained and is to be tested using the diagnostic instrument. Patient information may be entered, for example, by using a barcode reader which is functionally connected to the diagnostic instrument or the patient information may be manually entered by the operator using a keypad located on the diagnostic instrument.

After optionally entering a device instrument operator ID, the operator enters information regarding the test strip such as an assay name and type, a kit lot number, a cassette number and/or lot number, and an analyte name. After ensuring all necessary and relevant information is entered into the diagnostic instrument, the test strip with patient sample is placed into the diagnostic instrument according to manufacturer instructions and the assay is initiated. The diagnostic instrument analyzes the results of the assay and is capable of making a quantitative and/or qualitative measurement of the results. For example, a diagnostic instrument may assign a value of positive or negative to the presence or absence, respectively, of a line which is detectable at a specified wavelength measured by the diagnostic instrument. The results can then be saved in the memory of the device and/or on a temporary storage device such as a removable SD disk. The results are saved such that they remain linked with the information described above regarding the diagnostic instrument, the organization and facility, the operator and the patient.

Based on the test assay type discerned from the information on the bar code label or otherwise provided to the diagnostic device processor, the diagnostic device initiates an algorithm stored in the diagnostic device's memory for the assay for which the test device is designed, and/or based on user-defined selection of criteria.

The optics system in the diagnostic instrument can be an assembly of mechanical, electronic and optical components which serves to send light in the excitation wavelength range of the compound or analyte to be measured. The emitted light is measured by a detector, and a fluorescence value is displayed on the instrument. Light sources include xenon lamps, high pressure mercury vapor lamps, xenon-mercury arc lamps, lasers, and LED's. In one embodiment, the optics system of the diagnostic instrument illuminates the test strip with specific excitation with an ultraviolet light-emitting diode (UV LED) and then collects, processes and transforms the resulting europium fluorescence signal using a photodiode to an electronic signal that is converted by an analog-to-digital converter into useable analytical data.

In one embodiment, a calibration cassette is available for ensuring that the diagnostic instrument is properly reading and analyzing the results generated through use of the test strip as described above. An exemplary calibration cassette is described in U.S. Patent Pub. No. 2013/0230844 (see, for example, paragraphs [0068-0073], the contents of which are incorporated herein by reference in their entirety). Operation of an exemplary diagnostic instrument as described herein is described in greater detail in U.S. Patent Pub. No. 2013/0230844 (for example, see the section titled, "Operation of Apparatus," paragraphs [0088-0098], the contents of which are incorporated herein by reference in their entirety).

Each time a test strip is analyzed by a diagnostic instrument, a quality control assay can be run by the diagnostic instrument, or a calibration cassette can be analyzed. Again, the results of the quality control assay and/or calibration assay are saved to the hard drive of the instrument or to a removable memory device. After completion of the assay and results analysis within the diagnostic instrument, an application located on the diagnostic instrument initiates a program which results in the transmission of the information to a router. When a diagnostic strip is used to analyze a patient sample, a program associates the assay results with the patient and instrument information (see Table 1 below) and generates a unique data set. The information is stored in the instrument and, if present, an external drive such as an SD disk.

The diagnostic instrument is associated with and/or generates information regarding the diagnostic instrument, including one or more of the fields shown below in Table 1. Each piece of information is associated with a data tag for storage in a database.

TABLE 1

| Data Type | Example Data Tag (Field) |
|---|---|
| Diagnostic instrument | Diagnostic instrument serial number |
| | Instrument Type |
| | Registration Date |
| | Time Zone |
| | Firmware Revision |
| | Router Type |
| | Router ID |
| Facility Information | Facility Name |
| | Facility Address |
| | Facility City |
| | Facility Zip Code |
| | Facility County |
| | Facility State |
| | Facility Country |
| | Organization Name |
| | Site ID |
| | Contact Name |
| | Contact E-mail |
| | Contact Phone |
| | Date and Time of Storage |
| | Operator ID |
| Test Strip Information | Order Number |
| | Assay Name (Indication) |
| | Kit Lot Number |
| | Cassette Number |
| | Cassette Lot Number |
| | Assay Type (Assay Number) |
| | Analyte name |
| | Result Type |
| Patient Information | Patient ID |
| | Patient Age |
| | Patient Gender |
| | Patient Demographics |
| | Patient Status |
| Results Information | Result Type (diagnostic, QC, Calibration) |
| | LOINC Code (Logical Observation Identifiers Names and Codes) |
| | SNOMED Code |
| | Test Result |
| | Transmission Date and Time |
| | Test Flag (Final or Resent) |

Each diagnostic instrument used to run a diagnostic test is provided with a unique serial number at the time of manufacture. An "instrument type" identifier is also associated with each diagnostic instrument. When a diagnostic instrument is installed for use in a laboratory, it can be assigned a registration date, time zone, and firmware revision number. At the time of installation of a diagnostic instrument, the facility name and address can be stored in the memory of the diagnostic instrument as well as the name of the organization which owns or controls the diagnostic instrument. The name and contact information for an administrator or supervisor, for example, may also be saved within the memory of the diagnostic instrument. In one embodiment, the information is saved to a hard drive within the instrument. In another embodiment, the information is alternatively saved, or additionally saved to a temporary disk such as an SD disk/card or USB data storage device. The diagnostic instrument memory is also programmed to be customized with respect to the type of information which may be saved in association with a single diagnostic test. In other words, the owner of the instrument can program the diagnostic device to accept or require additional information which is then saved as a record to an owner-defined field.

The diagnostic instrument can assign each assay a unique identifier (e.g., primary key) and thereby associate each assay (unique identifier) with some or all of the patient information as well as with some or all of the facility and diagnostic instrument identifier information. Importantly, by associating each diagnostic assay with this information to form a data set, the data set can be made accessible to only designated users, such that only owners of individual data sets or users designated by the owners will have access to data sets which include the owner identification.

In preferred embodiments, the diagnostic instrument includes a program which is able to encrypt the test results, the user information, the patient information and/or the instrument information. The diagnostic instrument also includes a program which can de-identify the patient. In other words, the patient name and identifier number can be masked or deleted from each data set. Other patient information, such as age, can also be deleted or masked if desired. In one embodiment, patient age is replaced with an age range. For example, patients that are older than 80 years are assigned an age of ">80", or patients that are between the age of 50 and 60 years are assigned an age value of "50-60."

A diagnostic instrument used according to the methods described herein comprises a port to which a network cable may be connected. The network cable provides a wired connection between the diagnostic instrument and a router. Alternatively, a cable is used to connect the diagnostic instrument to a hub or switch which then allows a wired connection to both a router and a workstation which has a Laboratory Information Management System installed. Use of a hub or switch also allows one to connect multiple diagnostic devices to a single router (See, for example, FIGS. 2 and 3).

Once the assay results are obtained within diagnostic instrument x, the results are saved to the hard drive of the diagnostic instrument and/or to an external drive such an external hard drive, SD card or a flash drive.

As depicted in FIG. 1, the networked surveillance system includes a router 20 which receives a data set from a diagnostic instrument 10 each time a diagnostic assay is run and analyzed by diagnostic instrument 10, and then transmits this data set through a router 20 to a first remote server 30. Router 20 can receive data from the diagnostic instrument via a secure SSL TCP/IP connection. In preferred embodiments, the information is transmitted from diagnostic instrument 10 through a cable such as an Ethernet cable or fiber optic cable. In alternative embodiments, the information is transferred from the diagnostic instrument to the router by a wireless connection.

A router as used in the presently described system includes at least one or two Ethernet ports. A first Ethernet port is used to provide a connection to a diagnostic instrument. The connection between the router and the instrument may be direct, through a hub or switch, or through other indirect means. A second Ethernet port can be used to provide internet connectivity, for example, though a cellular modem a LAN.

The router is able to communicate with a first remote server via a cellular signal or via an internet (wired) connection. If for any reason the connection with the first remote server is interrupted, the router can buffer the encrypted data and send it to the first remote server when the connection is restored. The router includes configurable routing and switching capability. The router has worldwide cellular wireless compatibility (currently certified in at least 57 countries).

Data and test results generated by one or more diagnostic instruments as described herein to produce a data set are first transmitted to a router and then transmitted from the router to a first server where it is stored at least temporarily in a folder or other similar directory on the first server. In one embodiment, the first server is in a location remote from the one or more diagnostic instruments, however it will be appreciated that the first server need to be remote for functionality of the system. The system described herein is in the context of a system with a first remote server yet it is to be understood that that it is merely exemplary. This first remote server stores each of a plurality of data sets received from every diagnostic instrument to which the server has a connection via a router. The data sets are obtained via one or more routers as described above. Accordingly, the results and associated information are transmitted from the router to the first remote server each time (or on a regularly scheduled frequency such as once or twice per day, or more often if an infectious outbreak is occurring) a diagnostic test is performed and analyzed by a diagnostic instrument. In an alternative embodiment, one or more data sets are saved to a diagnostic instrument, and an application located within the diagnostic instruments runs on a schedule to initiate the transmission of the one or more data sets to the first server at a specified time(s) during each day.

The data sets which are transferred to the first (remote) server by numerous routers are stored in a secure directory to which only a designated authorized user has access. In one embodiment, the data sets are stored temporarily on the first remote server, i.e., the data sets are stored on the first remote server for at least 1 hour, but less than 24 hours, 48 hours, 72 hours, 1 week or 1 month. The data sets can be stored in a simple folder within a directory on the remote server. The data sets transmitted to the first remote server can be organized, for example, based on the owner of the diagnostic instrument, then by individual diagnostic instrument. The data sets of a particular owner can be segregated from data sets of different owners.

Data sets stored in the first remote server are subsequently transferred to an end user database server 40, to an end user work station 50 and/or to a second remote server (FIG. 1) to facilitate access by an end user 55. The continuing description is in the context of the system comprising an optional second remote server, however it will be appreciated that functionality of the system is achieved in the absence of the second remote server in favor of a direct communication between an end-user database server or end-user work station. The second remote server (or end-user database server or end-user work station) houses a software application which instructs the second remote server (or first server in the absence of a second server) to connect to the first remote server and to survey all data stored within the first database located on the first remote server and to identify any data which have not been previously transferred to the second remote server. Any and all new data are then transferred to a database housed on the second remote server. A cyclic redundancy check (CRC) is performed on the data saved to the second remote server. Access to these data is restricted to users which have been specified by an administrator of the second remote server, in one embodiment. In another embodiment, only the owner of a plurality of data sets can access the data sets. An administrator of the data base on the second remote server is able to access data sets belonging to all owners of all data sets.

All data sets which are transferred to the second remote server are stored within a second database housed on the second remote server. When individual data sets are saved to the database housed on the second remote server, an application on the second remote server runs which assigns to each data set a SNOMED identifier and a LOINC identifier, which thereby become associated with the data set.

The database located on the second remote server is designed to be secure and accessible only by a database administrator(s) and by users which have been granted access to the database. The second remote server can house multiple database instances. In one embodiment, a database on the second remote server receives and stores data sets belonging only to a single owner. In another embodiment, there are multiple second remote servers, each containing a database to store results received from diagnostic instruments via routers as described above.

In another embodiment the database on the second remote server is a flat-file database in which each diagnostic test result is stored in association with one or more of the parameters (also referred to herein as assay-associated data elements or values) listed in Table 1. In another embodiment, the database on the second remote server is a relational database.

The second remote server has both a reporting application and a query application. The reporting application will generate reports containing individual data sets belonging to one or more owners of the data sets, then send the reports to a designated end user apparatus. The query application provides in part an interface through which an end-user having access to the database can browse or query the data sets which are stored in the database on the second remote server.

The reporting application, e.g., a scheduled agent, is programmed to generate reports based on characteristics which have been selected by the end user, such name of the clinical laboratory that ran the diagnostic test, patient age, patient gender, and patient residence. The scheduled agent can be programmed to generate a report on a pre-determined and/or periodic basis. For example, the scheduled agent may transmit a report containing all new data sets owned by a specified owner at 08H00 UTC (coordinated universal time) each day. Other options for the timing of the transmission of a report include, but are not limited to, manually transmitting a report at any time on any day by an administrator or transmitting a report at a regular interval other than a 24-hour interval, such as every 12 hours. This flexibility of report transmission scheduling may be important, for example, during times of a pandemic or other recognized health-related crisis. Alternatively, or additionally, a user affiliated with a specified owner may send a request for a report generation of all new data at any time. The generated report can contain a plurality of clinical diagnostic results and the associated data for each diagnostic result. The information contained in a generated report can be determined by the end-receiver of the information. For example, a state health department may have a database designed to receive such a generated report. Accordingly, a report generated on the second remote server for transmission to this state health agency will contain information and will be formatted in such a way as to comply with the requirements of that state health department.

The report generated by the reporting application can have a variety of formats, including but not limited to a simple text file, a CSV file, or a PDF document. The information generated by the reporting application may be pasted into the body of an e-mail and e-mailed to the end-receiver of the information, or a file containing the information (e.g., text document, CSV file, PDF document) may be attached to the e-mail. In one embodiment, a file generated by the reporting application is uploaded (e.g. via an ftp client) to a server owned by the end-receiver of the report. In an alternative embodiment, the report generated by the reporting application may be of a format which can be received by an end-receiver database, and an application housed on the end-receiver server can transfer data within the report into a database located on the end-receiver server, such that individual data are assigned to the correct fields within the database.

The second remote server also houses a query application which can present a user interface for an end-user to design a report for generation. In this embodiment, the second remote server stores script programs which can be executed by a remote user. A remote user accesses and queries the second database from a remote workstation. In one embodiment, the remote workstation includes a web browser application which can access and interact with the second database located on the second remote server. The second remote server includes script programs which are executed by an end user operating a remote workstation. For example, a computer or workstation may include a web browser through which an end user remotely accesses and queries the database on the second remote server.

An end-user who has been granted access to the database on the second remote server will be able to query the database only for data sets owned by the owner with whom the end user is associated. In one embodiment, an end user having access to data sets associated with one or more diagnostic devices within the disease surveillance system is able to query the second database which contains all of the data sets generated and owned by the owner with whom the end user is affiliated. Through this interface and associated scripts housed on the second remote server, the end user can produce alternative data sets, generate custom reports, and/or generate graphical representations of the data sets. FIG. 6 shows an exemplary (artist's rendering) of an interface generated for access to the database on the second remote server (or on the first server if no second server is present). The interface can display data sets based on, for example, the time the clinical diagnostic assay was performed, the type of diagnostic assay which was run, the type of result, the name of the organization, the serial number of the diagnostic instrument, and/or the facility in which the diagnostic instrument(s) was located, including for example, county, state, country, zip code of the facility or diagnostic instrument. The data sets may be initially displayed in rows and columns. In such a display, the end user can manipulate the order in which the columns and rows are displayed. Each clinical diagnostic assay result may be selected to see details of the result including the LOINC and SNOMED codes, the patient information, information regarding the diagnostic assay kit used, information regarding the testing site, and information regarding the diagnostic instrument and owner.

Figure 7:
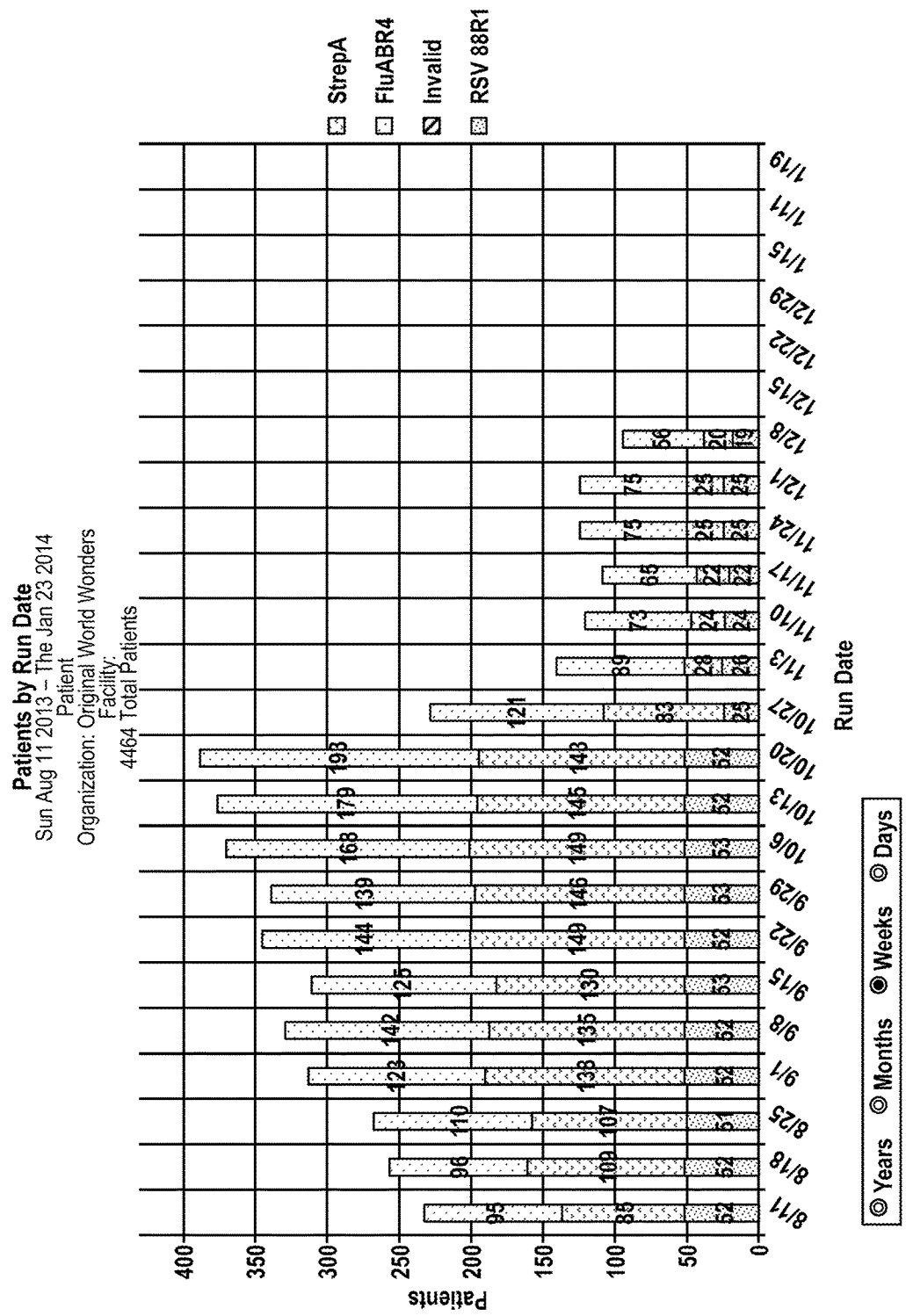
FIG. 7 shows an embodiment of output generated from a database on a server.

Further, the queried data may be displayed as a chart. For example, the data may be charted by run date (FIG. 7), diagnostic assay, result, result trend, percent positive, or test volumes by type (patient, quality control or calibration). Each chart display may also be manipulated to show results by days, weeks, months or years. When charting the data to show patient result trends, the chart may be further manipulated to show results for a single clinical diagnostic assay type (see FIGS. 8A-8B).

Figure 9:
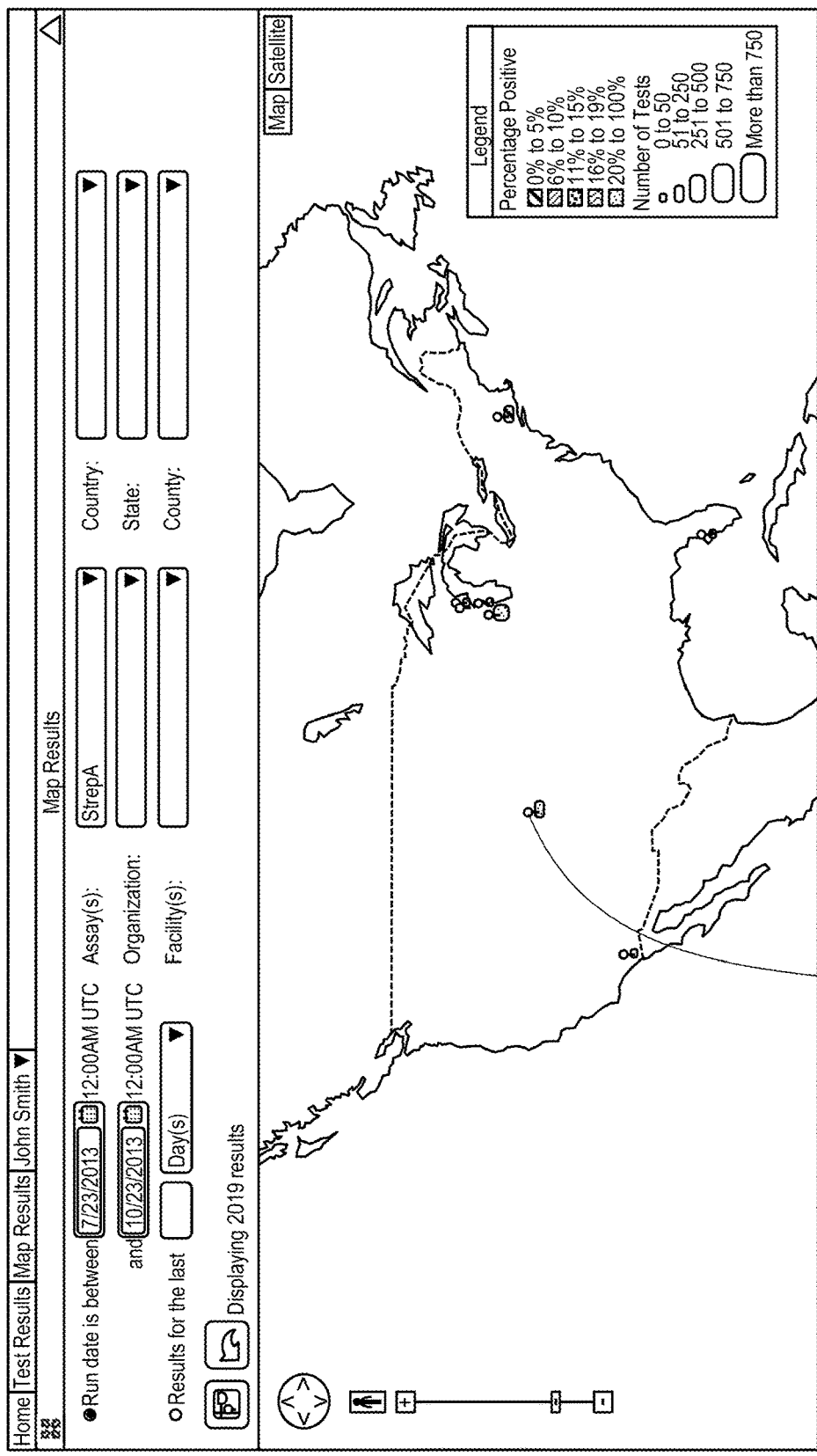
FIG. 9 shows an embodiment of output generated from a database on a server.

In a particular embodiment, the end user can query the database to generate a map of the geographical locations of each test result (e.g., location within a city, state or country) as shown in FIG. 9, which is an artist's rendering of a map of a portion of North America, showing Canada, the U.S. and a portion of Mexico. An end-user can query the database to present data from the dataset in graphical form according to state or province, according to zip code in which the test facility, instrument and/or patient sample was tested, the country, etc. Pins, such as pin 490, provide a visual indicator of a test result for easy viewing by an end user. Pins or color indicators can be used to indicate percent positive and the number of tests performed in locations by country, state, county, zip code, etc.

Figure 10:
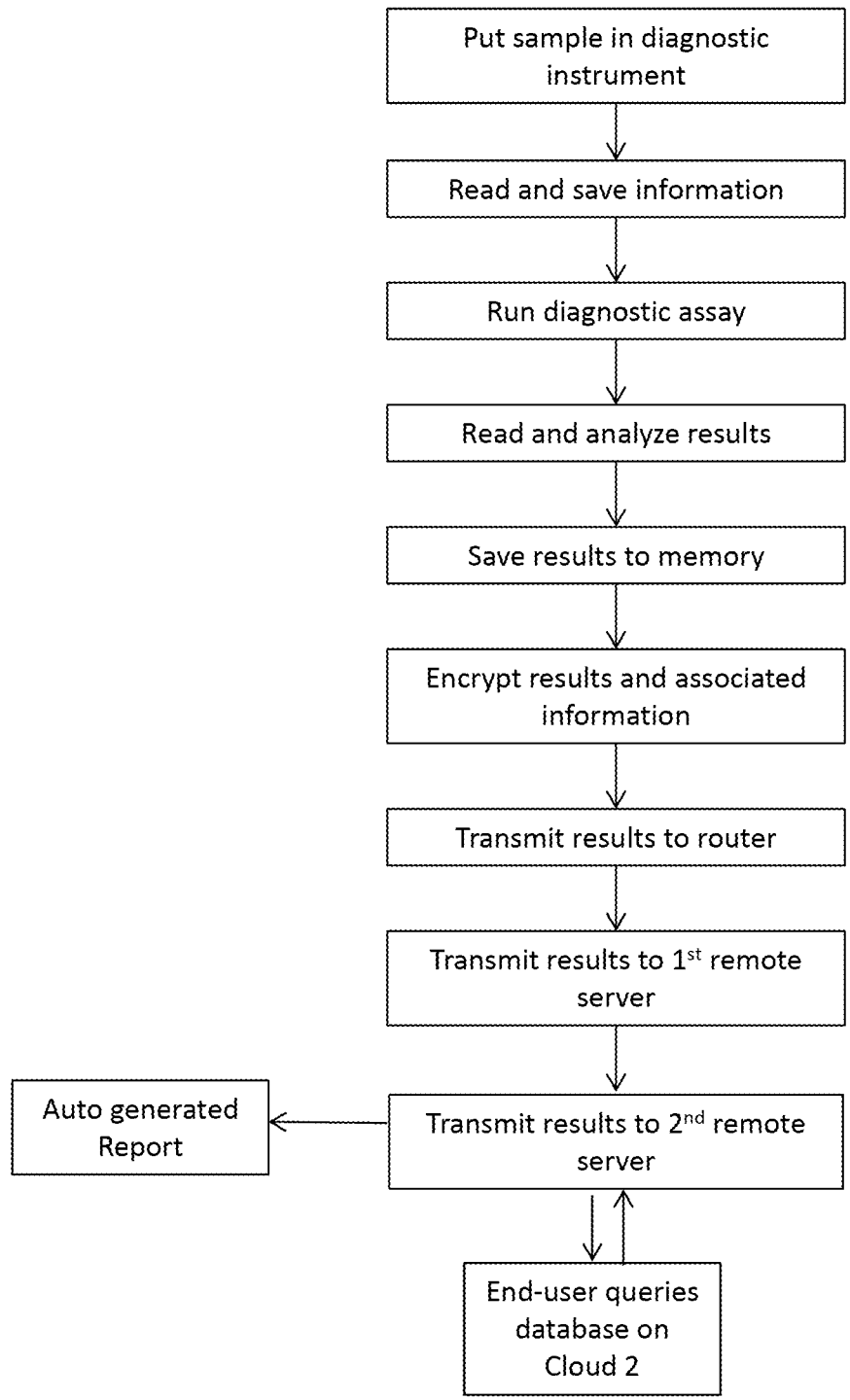
FIG. 10 is a flow diagram of the method steps to obtain, store and report data generated by a clinical diagnostic instrument.

FIG. 10 is a flowchart illustrating one embodiment wherein of the disease surveillance system (500) described herein. A patient sample is applied to a test strip or other clinical diagnostic assay device and placed into a diagnostic instrument (505) by an operator such as a healthcare technician or clinical assistant. Information regarding the diagnostic assay device, the diagnostic instrument, the owner of the diagnostic instrument, the patient or subject from whom the sample came is input into the diagnostic instrument (510). The diagnostic assay is performed by the diagnostic instrument (515), the results of the assay are detected and analyzed (520) and saved to the memory of the diagnostic instrument (525), wherein each diagnostic assay result is associated with the information input at 510 to form a data set. The data set are encrypted by an encryption application within the diagnostic instrument (530). In one embodiment, the patient is de-identified. An application within the diagnostic instrument is then triggered to transfer the data set to a router (535) and the router connects to the first remote server. If the router cannot connect to the remote server, the data set is saved in the router buffer until a connection to the first remote server is made. The data set is then transferred and saved to a database or directory on the first remote server and the data set is filed based on the owner and then by the diagnostic instrument serial number (540). On a periodic basis, the second remote server connects to the first remote server and runs an application which queries the appropriate directory on the first remote server to identify new data sets (data sets which have not previously been transferred to the second remote server (545). The new data sets are transmitted to the second remote server and saved to a database housed on the second remote server. The second remote server can have an application which is programmed to generate a report which contains data sets for a defined time period (e.g., the previous 24 hours). This report generally includes data sets associated with a single owner. The report is then sent to an end user designated by the owner of the data sets within the generated report (550). The database located on the second remote server is accessible by designated end users who may access only data sets owned by owners with whom the owners are affiliated. These end users can access the database on the second remote server through the internet using, for example, a web browser. The end user has access to an interface which allows the end user to query the database using forms and to generate custom reports (555).

It will be appreciated that the description of the servers as a first "remote" server or as a second "remote" server is exemplary, as in one embodiment the first and/or second server may be remote (e.g., in a different geographic location) from the diagnostic instrument or from other components of the system, however one or both servers can be in the same location in some situations.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A system, comprising:
a plurality of diagnostic instruments, each diagnostic instrument comprising:
a memory circuit storing an application comprising instructions;
a processing unit; and
a detector that interacts with a test assay, the processing unit configured to execute the instructions to:
(i) automatically associate the test assay with multiple values to generate a diagnostic, the diagnostic stored within a memory of the diagnostic instrument, the multiple values related to one or more of: a test assay identifier, a test assay result, a patient identifier, and a diagnostic instrument identifier, and
(ii) select a report transmission schedule from one of a regular interval option, a manual option, or an end user request; and
(iii) transmit, at a specified time on the report transmission schedule, the diagnostic to a first server for storage, wherein the first server generates a report based on the diagnostic from each diagnostic instrument in the plurality of diagnostic instruments, the report configured for display on a second server or on an end-user workstation, wherein the report transmission schedule is provided by the first server to the application in each diagnostic instrument indicating a frequency of transmitting the diagnostic to the first server, and wherein the first server is configured to increase the frequency of transmitting the diagnostic in an infectious outbreak event.

2. The system of claim 1, wherein at least one of the plurality of diagnostic instruments is configured to encrypt the diagnostic before transmit.

3. The system of claim 1, wherein a router receives the diagnostic from the diagnostic instrument and then transmits the diagnostic to the first server.

4. The system of claim 1, wherein the first server comprises a first memory storage which is designed to store multiple diagnostics generated by the diagnostic instrument.

5. The system of claim 1, wherein the end-user workstation is configured to query the first server to display the diagnostic upon receipt of a request from an end-user.

6. The system of claim 1, wherein the second server is configured to:
remotely receive the diagnostic transmitted by the first server, and
store the diagnostic in a second memory storage.

7. The system of claim 6, wherein the end-user workstation is configured to query the second server to display the diagnostic upon receipt of a request by an end-user.

8. The system of claim 6, wherein the second server is configured to transmit the report to the end-user workstation, wherein the report comprises a plurality of diagnostics, and wherein the end-user workstation is configured to provide a graphic display of the report.

9. The system of claim 1, wherein the first server is configured to transmit the report to the end-user workstation, wherein the report comprises a plurality of diagnostics, and wherein the end-user workstation is configured to graphically display the report.

10. The system of claim 1, wherein the diagnostic is transmitted to the first server using a cellular signal.

11. The system of claim 1, further comprising a laboratory workstation which houses a Laboratory Information System (LIS).

12. The system of claim 1, wherein at least one of the diagnostic instruments comprises an optics system.

13. A system, comprising:
a) a first diagnostic instrument comprising:
a memory circuit storing an application comprising instructions;
a processing unit; and
a detector to interact with a test assay that receives a sample from a patient, processing unit configured to execute the instructions to store results detected by the detector as it interacts with the test assay to generate a diagnostic, and to transmit the diagnostic to a server at a specified time on a schedule, wherein:
the diagnostic comprises a plurality of assay-associated elements including at least a test assay identifier, a diagnostic instrument identifier, and a test assay result, and
a report transmission schedule configured from one of a regular interval option, a manual option, or an end user request; and
b) a first server configured to:
receive the diagnostic from the first diagnostic instrument,
store the diagnostic in a memory,
assign a unique identifier to the diagnostic within a first plurality of diagnostics for a display;
transmit the report transmission schedule to the application in the first diagnostic instrument, the report transmission schedule including a frequency of transmitting the diagnostic; and
increase the frequency of transmitting the diagnostic in an infectious outbreak event.

14. The system of claim 13, further comprising:
a second server configured to:
generate a plurality of diagnostic information queries specific to an assay-associated element in the plurality of assay-associated elements; and generate a report containing at least partially the plurality of assay-associated elements based on a query.

15. The system of claim 13, further comprising a router configured to receive the diagnostic from the first diagnostic instrument and to transmit the diagnostic to the first server.

16. The system of claim 13, further comprising a second server comprising a memory configured to store the first plurality of diagnostics for the display.

17. The system of claim 13, further comprising a workstation that stores a laboratory information system (LIS), wherein the workstation is coupled with the first diagnostic instrument via a local area network.

18. The system of claim 13, wherein the plurality of assay-associated elements includes a residence or zip code of the patient or of the first diagnostic instrument, an age of the patient, and/or a gender of the patient.

19. The system of claim 13, wherein the display comprises a geographic map based on a residence or a zip code of the patient or of the first diagnostic instrument.

* * * * *